United States Patent [19]
Venugopalan et al.

[11] Patent Number: 5,246,930
[45] Date of Patent: Sep. 21, 1993

[54] 9-SUBSTITUTED COMPOUNDS OF 3α,
11α-EPOXY-3,4,5,5Aα,6,7,8,8A,9,11,11A-
UNDECAHYDRO-3β,6α,9-TRIMETHYL-
FURANO[3,4-J][1,2]BENZODIOXEPIN,
PROCESSES FOR THEIR PREPARATION
AND THEIR USE AS ANTIPROTOZOAL
AND ANTIVIRAL AGENTS

[75] Inventors: Bindumadhavan Venugopalan, Thane; Chintamani P. Bapat, Bombay; Pravin J. Karnik, Thane; Bansi Lal, Bombay; Dipak K. Chatterjee, Bombay; Subramani N. Iyer, Bombay; Jürgen Blumbach, Bombay, all of India

[73] Assignee: Hoechst Aktiengesellschaft, Frankfurt am Main, Fed. Rep. of Germany

[21] Appl. No.: 694,203

[22] Filed: May 3, 1991

[30] Foreign Application Priority Data

May 7, 1990 [EP] European Pat. Off. ........ 90108580.3

[51] Int. Cl.⁵ .................. A61K 31/535; A01N 43/58; C07D 321/00; C07D 413/00
[52] U.S. Cl. .................. 514/232.8; 514/253; 514/338; 514/348; 514/450; 544/148; 544/238; 544/378; 549/348
[58] Field of Search ............ 549/348; 514/450, 895, 514/232.8, 253, 338, 348; 544/148, 238, 378

[56] References Cited

U.S. PATENT DOCUMENTS 4,963,683 10/1990 Avery et al. .................. 549/348

FOREIGN PATENT DOCUMENTS 0330520  8/1989  European Pat. Off. ........... 549/348
0362730A1 4/1990 European Pat. Off. .
WO88/04660 6/3088 PCT Int'l Appl. .

OTHER PUBLICATIONS

Len et al., "Antimalarial Activity of New Water-Soluble Dihydroartemisinin Derivatives. 2.1,2, Stereospecificity of the Ether Side Chain", J. Med. Chem., 32, 1989, 1249–1252.

Primary Examiner—Bernard Dentz
Assistant Examiner—Raymond Covington
Attorney, Agent, or Firm—Finnegan, Henderson, Farabow, Garrett & Dunner

[57] ABSTRACT

Compounds of formula I

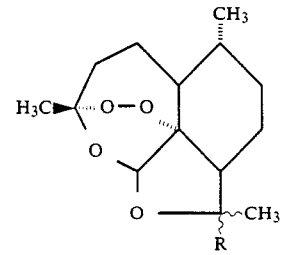

in which the substituted R has the given meaning, have an antimalarial and a antiviral activity.

7 Claims, No Drawings

9-SUBSTITUTED COMPOUNDS OF 3α, 11α-EPOXY-3,4,5,5Aα,6,7,8,8A,9,11,11A-UNDECAHYDRO-3β,6α,9-TRIMETHYL-FURANO[3,4-J][1,2]BENZODIOXEPIN, PROCESSES FOR THEIR PREPARATION AND THEIR USE AS ANTIPROTOZOAL AND ANTIVIRAL AGENTS

The invention relates to novel 9-substituted compounds of 3α,11α-Epoxy-3,4,5,5aα,6,7,8,8a,9,11,11a-undecahydro-3β,6α, 9-trimethylfurano[3,4-j][1,2]benzodioxepin, pharmaceutically acceptable salts thereof and processes for their preparation and their use against protozoal and viral infections.

9-Substituted 3α,11α-Epoxy-3,4,5,5aα,6,7,8,8a,9,11,-11a-undecahydro-3β,6α,9-trimethylfurano[3,4-j][1,2]benzodioxepin compounds of the invention are represented by the general formula I $$\text{(I)}$$

wherein R stands for
CHO;
COOR$_1$,
  wherein R$_1$ stands for hydrogen, alkyl, substituted alkyl, alkenyl, substituted alkenyl, alkynyl, substituted alkynyl group;
CH$_2$OR$_2$,
  wherein R$_2$ stands for hydrogen, alkyl, substituted alkyl, alkenyl, substituted alkenyl, alkynyl, substituted alkynyl, dialkylamino alkyl group or 3α,12α-Epoxy-3,4,5,5aα,6,7,8,8aα, 9,10,12β,12a-dodecahydro-3β,6α,9β-trimethylpyrano[4,3-j][1,2]benzodioxepin-10-yl or a group COR$_3$, wherein R$_3$ stands for alkyl, substituted alkyl group, or a group SO$_2$R$_4$, wherein R$_4$ stands for alkyl or aryl group, or a group $$\underset{X}{\overset{\parallel}{C}}NR_5R_5',$$

wherein
X denotes O or S,
R$_5$ stands for hydrogen,
R$_5'$ stands for alkyl or aryl group or
NR$_5$R$_5'$, stands for heterocycle;
CONR$_6$R$_7$,
  wherein R$_6$ stands for hydrogen, aralkyl, R$_7$ stands for hydrogen, alkyl, aryl, aralkyl group or R$_6$ and R$_7$ together with the nitrogen to which they are attached form a heterocycle which may contain an additional hetero atom and is optionally substituted at one or more places;
CH=CR$_8$R$_9$,
  wherein R$_8$ stands for hydrogen, carboxyalkyl and R$_9$ stands for carboxyalkyl, aryl or heterocycle;
COSR$_{10}$,
  wherein R$_{10}$ stands for alkyl, substituted alkyl or aryl groups; and pharmaceutically acceptable salts thereof.

In the formulae presented herein the various substituents are illustrated as joined to furano (3,4-j)(1,2)benzodioxepin nucleus by one or two notations, a solid line (—) indicating a substituent in which is in the β-orientation (i.e. above the plane of the molecule) and a broken line (---) indicating a substituent which is in the α-orientation (i.e. below the plane of the molecule). The formulae have all been drawn to show the compounds in their absolute configuration. In as much as the starting materials having furano-(3,4-j)(1,2)-benzodioxepin nucleus are derived from naturally occurring materials, they as well as the final products have a furano(3,4-j)(1,2)benzodioxepin nucleus in the single absolute configuration depicted herein. The processes of the present invention, however, are intended to apply as well to the synthesis of furano(3,4-j)(1,2)benzodioxepines of the racemic series.

In addition to the optical centers of furano(3,4-j)(1,2)-benzodioxepin nucleus, the substituents thereon may also contain chiral centers contributing to the optical properties of the compounds of the present invention and providing a means for the resolution thereof by conventional methods, for example, by the use of optically active acids. A wavy line (~) indicates that substituents can either be in the α-orientation or β-orientation. The present invention comprehends all optical isomers and racemic forms of the compounds of the present invention where such compounds have chiral centers in addition to those of the furano(3,4-j)(1,2)benzodioxepin nucleus.

The term alkyl stands for C$_1$-C$_8$ straight or branched chain carbon compounds such as methyl, ethyl, propyl, butyl, isopropyl, t-butyl. The term alkenyl stands for straight or branched chain carbon compounds containing one or more double bonds. Suitable examples are acryl, stearyl, cinnamyl.

The term alkynyl stands for straight or branched chain carbon compounds containing one or more triple bonds and may in addition contain a double bond. Examples of alkynyl groups are 3-methyl-1-pentynyl, 1-butynyl, 3-methyl-1-butynyl, 2-butynyl-1-hydroxymethyl.

Substituents of substituted alkyl, alkenyl and alkynyl are halogen, hydroxy, carboxy, nitrile, acyl, aryl, heterocycle or a group NR$_6$R$_7$, wherein R$_6$ and R$_7$ are as defined above.

The term aryl stands for a phenyl group which is optionally substituted by one or more substituents such as halogen, alkyl, nitro, amino, hydroxy, alkoxy, carboxy, alkylcarboxylate, trifluoromethyl, substituted amino, acetyl, alkenyloxy, alkynyloxy. The term heterocycle stands for a cyclic group containing one or more hetero atoms such as piperazino, morpholino, piperidino, pyrrolidino, phthalimido, optionally substituted at one or more places by alkyl, alkoxy, hydroxy, halogen or aryl groups.

Preferred compounds of the invention are listed in Table 1.

Further preferred compounds of the invention are those of formula I, wherein R stands for a group CHO or CH$_2$OR$_2$, wherein R$_2$ has the same meaning as defined above.

Particularly preferred compounds of the invention are

3α,11α-Epoxy-3,4,5,5aα,6,7,8,8a,9,11,11a-undecahydro-9-formyl-3β,6α,9-trimethylfurano[3,4-j][1,2]benzodioxepin, 3α,11α-Epoxy-3,4,5,5aα,6,7,8,8a,9,11,11a-undecahydro-9-(2-propynoxy)methyl-3β,6α,9-trimethylfurano[3,4-j][1,2]-benzodioxepin, 3α,11α-Epoxy-3,4,5,5aα,6,7,8,8a,9,11,11a-undecahydro-9-(2-propenoxy)methyl-3β,6α,9-trimethylfurano[3,4-j][1,2]-benzodioxepin, 3α,11α-Epoxy-3,4,5,5aα,6,7,8,8a,9,11,11a-undecahydro-9-(p-toluenesulfonyloxy)methyl-3β,6α,9-trimethylfurano[3,4-j][1,2benzodioxepin, 3α,11α-Epoxy-3,4,5,5aα,6,7,8,8a,9,11,11a-undecahydro-9-(4-chlorophenylaminothiocarbonyloxy)methyl-3β,6α,9-trimethylfurano[3,4-j][1,2benzodioxepin, 3α,11α-Epoxy-3,4,5,5aα,6,7,8,8a,9,11,11a-undecahydro-9-(4-fluorophenylaminothiocarbonyloxy)methyl-3β,6α,9-trimethylfurano[3,4-j][1,2]benzodioxepin, 3α,12α-Epoxy-3,4,5,5aα,6,7,8,8aα,9,10,12β,12a-dodecahydro-10α-[3α,11α-epoxy-3,4,5,5aα,6,7,8,8a,9,11,11a-undecahydro-3β, 6α,9-trimethylfurano[3,4-j][1,2benzodioxepin-9-methylen]oxy-3β,6α,9β-trimethylpyran[4,3-j][1,2]benzodioxepin and 3α,12α-Epoxy-3,4,5,5aα,6,7,8,8aα,9,10,12β,12a-dodecahydro-10β-[3α,11α-epoxy-3,4,5,5aα,6,7,8,8a,-9,10,11,11a-undecahydro-3β,6α,9-trimethyl-furano[3,4-j][1,2]benzodioxepin-9-methylene]oxy-3β,6α,9β-trimethylpyrano[4,3-j][1,2]benzodioxepin.

TABLE 1

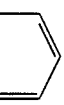

| R | M.P. °C. | % Yield |
|---|---|---|
| CHO | 100 | 85 |
| CH₂OH | 135-136 | 72 |
| COOH | 166-167 | 76 |
| CH₂OCH₂CH₂N(C₂H₅)₂ | Oil | 47 |
| CH₂OCH₂C≡CH | 105 | 71 |
| CH₂OCH₂CH=CH₂ | Oil | 45 |
| 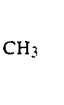 | Oil | 43 |
|  | Oil | 42 |
| 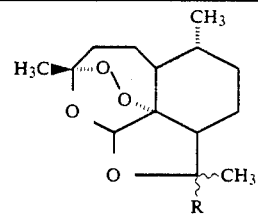 | Oil | 36 |
| 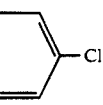 | Oil | 33 |
| 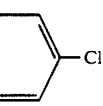 | Oil | 27 |
| CH₂OSO₂CH₃ | 123 | 42 |

TABLE 1-continued

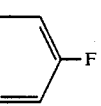

| R | M.P. °C. | % Yield |
|---|---|---|
| 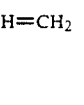 | 160 | 42 |
| 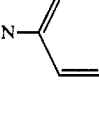 | 89-90 | 42 |
|  | 79-80 | 37 |
| CH₂OCNHCH₂CH=CH₂ (‖S) | Oil | 23 |
| 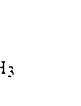 | 69-71 | 22 |
| 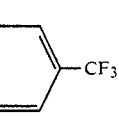 | Oil | 43 |
| 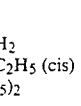 | 93 | 43 |
| 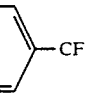 | 170-172 | 25 |
| COOCH₂CH₂Cl | 112 | 46 |
| COOCH₂CH=CH₂ | Oil | 38 |
| CH=CH—COOC₂H₅ (cis) | Oil | 54 |
| CH=C(COOC₂H₅)₂ | Oil | 22 |
|  (cis) | Oil | 27 |
| COS—C₆H₅ | Oil | 26 |
| COOCH₂CH₂Br | Oil | 47 |
| COOCH₂CH₂CH₂Cl | Oil | 24 |
| COOCH₂(CH₂)₆CH₂Cl | Oil | 21 |
| COOCH₂CH₃ | Oil | 29 |

TABLE 1-continued

[Structure: tricyclic endoperoxide with CH3, H3C, O-O bridge, and substituent OCH2-R pendant; R position on terminal carbon]

| R | M.P. °C. | % Yield |
|---|---|---|
| [structure with OCH2— attached, CH3, H] | 100 | 21 |
| [structure with OCH2— attached, CH3, H stereochemistry] | 154-156 | 34 |

TABLE 1-continued

[Structure: tricyclic endoperoxide with CH3, H3C, O-O bridge, and O-CH(R)-CH3 pendant]

| R | M.P. °C. | % Yield |
|---|---|---|
| CH2O—⟨N=N⟩—Cl | 150-152 | 72 |
| CH2OCOH | 84 | 55 |
| CH2OCOOH | 98-99 | 36 |
| CH2OCO—⟨C6H4⟩—NO2 | 158-159 | 64 |
| CH2OC(=S)NH—⟨C6H5⟩ | 81-82 | 44 |
| CH2OC(=S)NH—⟨C6H3(Cl)(COOC2H5)⟩ | oil | 27 |

The process for the preparation of compounds of the invention comprises the reaction sequence outlined in the scheme 1 wherein $R_1$, $R_2$, $R_3$, $R_4$, $R_5$, $R_6$, $R_7$, $R_8$, $R_9$ have the same meaning as described above.

The process comprises treatment of compounds of the formula II [prepared as reported in J. Med. Chem. 1989, 32, 1249-1252] with a brominating agent, preferably with liquid bromine using halogenated hydrocarbon as solvent such as carbon tetrachloride and preferably stirred for a period of one hour, then quenching with water and isolating the product of formula III from the organic layer as described herein.

Scheme 1
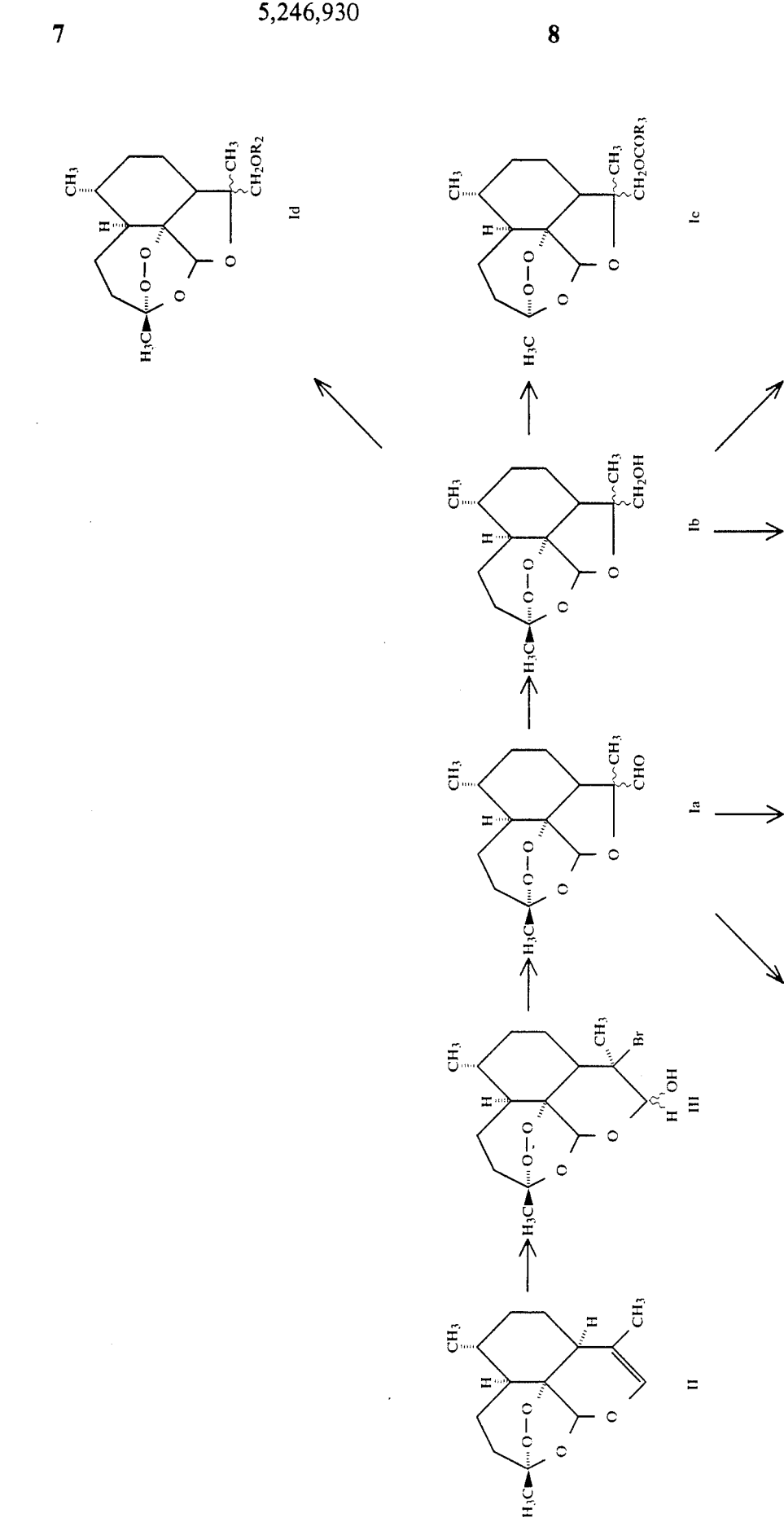

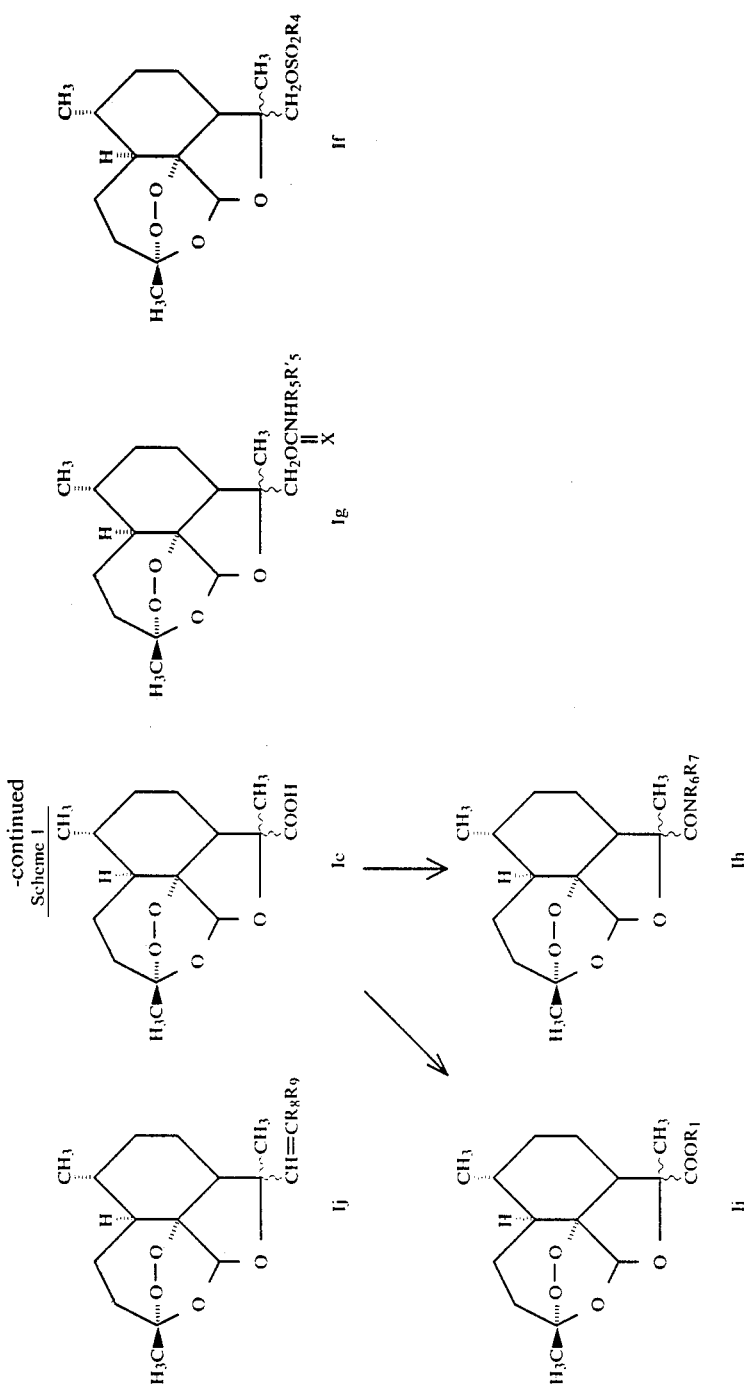

The preparation of compounds of the formula Ia comprises treating compounds of formula III with an organic base preferably such as triethylamine, diethylamine, benzylamine or diazabicycloundecene preferably with diazabicycloundecene using organic solvent such as halogenated hydrocarbons such as chloroform, methylene chloride, carbon tetrachloride at temperatures ranging from 0° to 37° C., preferably at 27°-30° C. for a period of 15 minutes to 60 minutes preferably for forty to forty five minutes. Reaction mixture is then worked up by concentration under vacuum and the residue obtained is purified by chromatography on adsorbent such as silica gel and using eluent such as chloroform to obtain compounds of the formula Ia.

Compound of the formula Ib is prepared from compound of formula Ia by treatment with reducing agents preferably such as sodium borohydride using alcohols such as ethanol, methanol, isopropanol as solvents, preferred being ethanol at temperatures ranging from 0° to 30° C. preferably at 27°-30° C. for a period of 15 minutes to 60 minutes preferably for thirty minutes. After the completion of reaction mixture is treated with aqueous solution of ammonium chloride and then concentrated under vacuum to remove ethanol. Residue is extracted with organic solvents such as ethylacetate, chloroform, dichloromethane. Organic layer is then separated and washed with water, dried over drying agents such as sodium sulfate and then concentrated. The residue obtained is purified by chromatography preferably over silica gel using eluant such as mixture of ethylacetate and chloroform to obtain compound of the formula Ib.

Compound of the formula Ic is obtained from compound of the formula Ia by treatment with oxidising agents preferably such as aqueous silver nitrate solution in the presence of an aqueous alkaline solution such as sodium hydroxide or potassium hydroxide and an organic water miscible solvent such as ethanol, methanol preferably being ethanol at temperatures from 0° C. to 45° C., preferred being 27°-30° C. for a period from one hour to six hours, preferably for two hours. The reaction mixture is then filtered, concentrated and the residue is extracted with organic solvents such as ethylacetate or halogenated hydrocarbons such as chloroform, methylenechloride. Extracts after washing with water are dried over drying agents such as sodium sulfate and then concentrated. Residue obtained is purified either by crystallisation or by chromatography to obtain compounds of the formula Ic.

Compounds of the formula Id, wherein $R_2$ has the same meaning as defined earlier except 3α,12α-Epoxy-3,4,5,5aα,6,7,8,8aα,9,10,12β,12a-dodecahydro-3β,6α,9β-trimethylpyrano[4,3-j][1,2]benzodioxepin-10-yl are prepared from compound of formula Ib by alkylation, preferably in the presence of a base such as sodium hydride in an anhydrous organic solvent such as benzene, toluene or dimethyl formamide, preferably dimethylformamide and halide of the formula $R_2X'$, wherein $R_2$ has the same meaning as defined above and $X'$ stands for halogen such as chloro or bromo at temperatures initially ranging from 0° C. to 30° C., preferably at 0°-5° C. for a period from 5 minutes to 60 minutes preferably for 10-15 minutes and then at temperature 27° C. for a period of one to six hours preferably for two hours. Reaction mixture after dilution with water is extracted with organic solvents such as petroleum ether, chloroform, ethylacetate and extracts after treatment with water and drying agents are concentrated and purified by column chromatography but in the case of compounds wherein $R_2$ has a basic group, reaction mixture is purified from organic solvent extract by acid base treatment to obtain compounds of the formula Id.

Compounds of the formula Id wherein $R_2$ stands for 3α,12α-Epoxy-3,4,5,5aα,6,7,8,8aα,9,10,12β,12a-dodecahydro-3β,6α,9β-trimethylpyrano[4,3-j][1,2]benzodioxepin-10-yl are also prepared from compound of the formula Ib by treatment with dihydroartemisinin, preferably in the presence of a catalyst such as borontrifluoride etherate at 0° C. using organic solvent such as anhydrous methylene chloride for a period of fifteen minutes to one hour. The product is isolated from the reaction mixture by washing the reaction mixture with water, drying the organic layer, filtering and concentrating the filtrate under vacuum. Final purification is done by flash column chromatography using silica gel column to obtain α and β isomers.

Compounds of the formula Ie are prepared from compound Ib by treatment with a mixture of acid chlorides of the formula $R_3COCl$, wherein $R_3$ has the same meaning as defined above, preferably in the presence of an organic base such as N,N-dimethylaminopyridine, triethylamine or pyridine preferred being N,N-dimethylaminopyridine in organic solvent such as chloroform or dichloromethane at temperatures ranging from 0° to 35° C., preferably at 27°-30° C. for a period of one hour to six hours preferably for three hours. The reaction mixture is then diluted with water, extracted with organic solvent such as petroleum ether and petroleum ether extract is then washed with dilute hydrochloric acid followed by water and dried over anhydrous sodium sulphate and then concentrated. Residue is purified by chromatography to obtain compounds of the formula Ie.

Compounds of the formula If are prepared from compound of formula Ib by treatment with compound of formula $R_4SO_2Cl$ preferably in pyridine wherein $R_4$ has the same meaning as defined earlier at temperatures ranging from 50° to 120° C., preferably at 90°-100° C. for a period of one to six hours, preferably for three hours. The reaction mixture after cooling to room temperature is diluted with water followed by extraction with organic solvents such as ethylacetate.

The ethylacetate extract is washed with dilute acetic acid, water, aqueous sodium bicarbonate and water in sequence and dried over anhydrous sodium sulfate and then concentrated after filtration to get residue which is purified by chromatography over silica gel to get compounds of formula If.

Compounds of the formula Ig are prepared from compound Ib by treatment with compounds of formula $R_5NCX$ in an organic base such as triethylamine, diethylamine, benzylamine, N,N'-dimethylpyridine or pyridine, preferably in pyridine wherein X stands for O or S and $R_5$ has the same meaning as defined above, at temperatures ranging from 30° to 80° C., preferably at 60° C. for four hours to sixteen hours, preferably for fourteen hours. The reaction mixture preferably is then cooled to room temperature and diluted with water and extracted with organic solvent such as petroleum ether, ethyl acetate or chloroform. The organic layer is then separated washed with dilute ice cold hydrochloric acid followed by water, dried over anhydrous sodium sulfate and concentrated under vacuum to obtain residue which is purified preferably by chromatography over silica gel to obtain compounds of the formula Ig.

Compounds of the formula Ih, wherein $R_6$, $R_7$ have the same meaning as defined earlier are preferably obtained from compound Ic by treatment first with thionylchloride in organic solvent such as ethylacetate at temperatures ranging from 0° to 30° C., preferably at 10°-19° C. for a period of half an hour and subsequent treatment of the mixture with an amine of the formula $NR_6R_7$ wherein $R_6$ and $R_7$ have the same meaning as defined earlier. The temperature of the reaction mixture may be raised to 60°-70° C. and maintained for half an hour. The reaction mixture is then cooled to room temperature, diluted with water and extracted with organic solvents such as petroleum ether. The organic extract is washed with water, dried over sodium sulfate and concentrated to obtain a residue which is repeatedly extracted with hot pentane to obtain compounds of the formula Ih.

Compounds of the formula Ii wherein $R_1$ has the same meaning as defined earlier are preferably prepared from compound Ic by treatment with thionyl chloride in dry ethyl acetate at room temperature for half an hour followed by treating the mixture with pyridine in ethylacetate at temperatures 0°-5° C. for fifteen minutes and then with alcohols of the formula $R_1OH$ wherein $R_1$ has the same meaning as defined above maintaining the temperature at 0° to 5° C. for further one hour. The reaction mixture is then extracted with organic solvent such as methylene chloride and the extract is washed with water, dilute hydrochloric acid and water and then concentrated after drying over drying agents such as sodium sulfate. Residue obtained is purified by flash chromatography using adsorbent such as silica gel and eluant such as chloroform, ethyl acetate to get compounds of the formula Ii.

Compound of the formula Ij wherein $R_8$ and $R_9$ stand for carbethoxy is preferably prepared from compound Ia by treatment with a mixture of compounds of formula $CH_2R_8R_9$ wherein $R_8$ and $R_9$ are as defined above, pyridine and piperidine and heating the resulting mixture at 60° to 100° C. preferably at 80° C. for a period of 10 to 24 hours preferably 16 hours. The reaction mixture on cooling is treated with dilute hydrochloric acid, extracted with petroleum ether and organic extract after washing with water, drying over sodium sulfate is concentrated and the residue obtained is purified by flash chromatography over silica gel to get compound of the formula Ij.

Compound of the formula Ij wherein $R_8$ stands for hydrogen and $R_9$ stands for the meaning described above are preferably prepared from compound Ia by treatment with phosphoniumylides of formula $Ph_3P=CHR_9$ wherein $R_9$ has the same meaning as above, at room temperature for two hours. The product is isolated by dilution with water, followed by extraction with chloroform. Chloroform extract is concentrated and residue obtained, purified by flash chromatography over silica gel using chloroform as eluant to obtain desired compound of the formula Ij.

The compounds of the instant invention may be of great use in the chemotherapy of human malaria and viral infections. They have shown moderate to excellent antimalarial activity against both chloroquine sensitive and resistant strains of rodent malaria.

The compounds of formula I may be administered in different manners, preferably perorally or parenterally in doses ranging from 2.5 to 100 mg/kg of body weight. As antimalarial drugs dosage unit forms such as dragees or capsules for oral administration or solutions and suspensions respectively for injections, each containing 100 to 400 mg of active substance are preferred. Such dosage units are administered once to three times daily depending upon the condition of the patient.

For oral administration, there may be used in particular tablets, dragees, capsules, powders or granules which contain the active substance together with the usual carriers, adjuvants and/or excipients such as starch, cellulose powder, talcum, magnesium stearate, sugar, gelatin, calcium carbonate, finely divided silicic acid, carboxymethyl cellulose or similar substances.

For parenteral administration, in particular for intramuscular injections, there may be used sterile suspensions for example oily suspensions prepared with the use of sesame oil, vegetable oil, castor oil or synthetic triglycerides, optionally with simultaneous use of surface active substances such as sorbitan fatty acid esters. Furthermore, there may also be used aqueous suspensions prepared for example with the use of ethoxylated sorbitan fatty acid esters, optionally with addition of thickeners such as polyethylene glycol or carboxymethyl cellulose.

Biological Evaluation Methodology

A. For Antimalarial Activity

The evaluation of blood-schizontocidal activity "28-day test" described by Raether and Fink [W.H.O. Report on the Scientific Working Group on the Chemotherapy in Malaria, TDR/Chemal 3rd Review, 85.3, Geneva, 3-5 Jun. 1985 and references contained therein] was followed.

Mice: All experiments were carried out in random bred male and female Swiss mice obtained from the Hoechst India Limited breeding house at Mulund, Bombay. The animals were free from Eperythrozoon coccoides. The animals received food pellets and water ad lib and were kept at 22°-25° C. room temperature.

Parasite: Plasmodium berghei K-173 strain drug-sensitive and berghei (NS) moderately resistant to chloroquine were obtained from the London School of Hygiene and Tropical Medicines. The strains produce lethal infection at $1 \times 10^7$ parasitized red blood cells per mouse when inoculated either intraperitoneally or intravenously, between 6 to 7 days post infection.

Administration of compounds: The compounds were administered orally or subcutaneously as per methods described by Raether and Fink [W.H.O. Report of the Scientific Working Group on the Chemotherapy in Malaria, TDR/Chemal 3rd Review, 85.3, Geneva, 3-5 Jun. 1985 and references contained therein].

Compounds of the invention were homogenized in double refined Kardi oil or peanut oil or corn oil with one or two drops of polyoxyethylenesorbitan monooleate (( ®)Tween.80, Sigma Chaniallo, England) and such suspensions were used for subcutaneous inoculation in mice. Drugs were administered for 5 days. 1st dosing was done within 2 hours of infection (D+0) followed by D+1, D+2, D+3 and D+4.

Observation of the treated mice: The blood smears were prepared at different intervals from D+4 and continued up to D+28. Blood smears were drawn from the terminal end of the tail and stained in Giemsa. Mice which were free from berghei on D+28 were considered as completely cured.

Results obtained with the compounds of Formula I of the invention are listed in Table 2.

TABLE 2

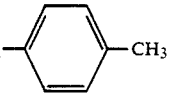

| R | Dose mg/kg × 5 | Route | Activity No. of animals cured/treated D + 7 | No. of animals cured/treated D + 28 |
|---|---|---|---|---|
| CHO | 25 | s.c. | 4/4 | 4/4 |
| $CH_2OCH_2C\equiv CH$ | 10 | s.c. | 6/6 | 2/6 |
| $CH_2OCH_2CH=CH_2$ | 5 | s.c. | 6/6 | 6/6 |
| 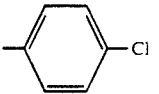 | 5 | s.c. | 5/6 | 1/6 |
| 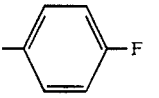 | 5 | s.c. | 12/12 | 12/12 |
|  | 2.5 | s.c. | 6/6 | 3/6 |
|  | 25 | p.o. | 6/6 | 6/6 |
|  | 5 | s.c. | 5/5 | 6/6*) |
|  | 2.5 | s.c. | 5/5 | 2/5*) |
|  | 25 | p.o. | 5/5 | 5/5*) |
|  | 5 | s.c. | 6/6 | 6/6 |
| 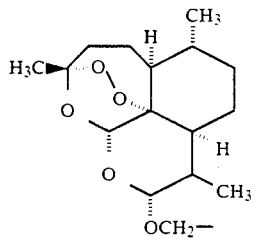 | 2.5 | s.c. | 12/12 | 12/12 |
|  | 1.25 | s.c. | 11/11 | 9/11 |
|  | 25 | p.o. | 6/6 | 5/6 |
|  | 5.0 | s.c. | 8/8 | 8/8*) |
|  | 2.5 | s.c. | 8/8 | 7/8*) |
| 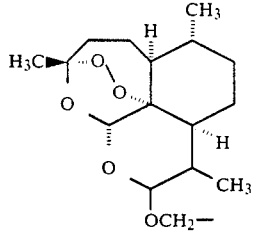 | 5 | s.c. | 5/5 | 5/5 |
|  | 2.5 | s.c. | 5/5 | 5/5 |
|  | 25 | p.o. | 6/6 |  |
|  | 5 | s.c. | 6/6*) |  |
|  | 2.5 | s.c. | 6/6*) |  |

Activity reported for all compounds is against chloroquine sensitive strain (*P. berahei* X-173). Activity reported with * is against chloroquine resistant strain.

B. For Antiviral Activity

Infection is given to Swiss mice (25 g body weight) either by intravenous or by intraperitoneal route with Friend's leukemia virus collected from serum of the previously infected mice diluted (1:50) with sterile Dulbecco's buffer saline.

The compounds were administered either by subcutaneous or intramuscular or oral or intraperitoneal route. The treatment started two days prior to the infection and continued for 8 more days post infection. Autopsy was done 2 days after the drug administration was over.

The compounds were tested against Friend's leukemia virus infection in mice and showed activity at a dose of 1 to 5 mg/mouse/day for 10 days. The reduction of the spleen weight as compared with the infected untreated control was considered as activity. The results indicate that such compounds may be active against Human Immunodeficiency Virus (HIV) infection in man.

The following examples illustrate the invention but do not limit the scope of the invention.

EXAMPLE 1

3α,11α-Epoxy-3,4,5,5aα,6,7,8,8aα,9,10,12β,12a-dodecahydro-9-bromo-10-hydroxy-3β,6α,9-trimethylpyrano[4,3-j][1,2]benzodioxepin To the solution of 3α,12α-Epoxy-3,4,5,5aα,6,7,8-,8aα,12β,12a-decahydro-3β,6α,9-trimethylpyrano[4,3-j][1,2]benzodioxepin-9-ene (1.0 g) in carbon tetrachloride (100 ml), water (0.5 ml) was added. To this stirred solution liquid bromine was added dropwise with a capillary tube until a pale bromine colour was persistant. The reaction mixture was stirred for further 1 hr. The reaction mixture was diluted with carbontetrachloride (100 ml), washed with water, dried (Na$_2$SO$_4$) and solvent removed under vacuum. The solid obtained was purified by flash chromatography over silica gel. Elution with ethyl acetate/chloroform gave the product after concentration of eluants, m.p. 124°–125° C. (d) Yield 79%.

EXAMPLE 2

3α,11α-Epoxy-3,4,5,5aα,6,7,8,8aα,9,11,11a-undecahydro-3β,6α,9-trimethylfurano[3,4-j][1,2]benzodioxepin-9-carboxaldehyde To the solution of 3α,11α-epoxy-3,4,5,5aα,6,7,8-,8aα,9,10,12β,12a-dodecahydro-9-bromo-10-hydroxy-3β,6α,9-trimethylpyrano[4,3-j][1,2]benzodioxepin (0.19 g) in chloroform (5 ml), diazabicycloundecene (DBU, 0.2 ml) was added at room temperature. The reaction mixture was stirred for 45 minutes, solvent was then removed under vacuum and the residue was purified by chromatography over silica gel using chloroform as an eluant to give 0.13 g of the title product in first few fractions; m.p. 100° C., yield 85%.

EXAMPLE 3

3α,11α-Epoxy-3,4,5,5aα,6,7,8,8a,9,11,11a-undecahydro-9-hydroxymethyl-3β,6α,9-trimethylfurano[3,4-j][1,2]benzodioxepin To the solution of 3α,11α-epoxy-3,4,5,5aα,6,7,8-,8a,9,11,11a-undecahydro-3β,6α,9-trimethylfurano[3,4-j][1,2]benzodioxepin-9-carboxaldehyde (1.0 g) in ethanol (60 ml), sodium borohydride (0.1 g) was added. The reaction mixture was stirred for 30 mins. Aqueous ammonium chloride was then added to decompose the excess of NaBH$_4$. Ethanol was removed under vacuum and the product was extracted with dichloromethane (3×25 ml). Combined dichloromethane extract was washed with water, aqueous sodium chloride, dried (Na$_2$SO$_4$) and solvent removed. The product was purified by flash chromatography over silica gel using 8% ethyl acetate in chloroform as an eluant to get the product, m.p. 135°–136° C.; yield 72%.

EXAMPLE 4

3α,11α-Epoxy-3,4,5,5aα,6,7,8,8a,9,11,11a-undecahydro-3β,6α,9-trimethylfurano[3,4-j][1,2]benzodioxepin-9-carboxylic acid To the stirred solution of 3α,11α-Epoxy-3,4,5,5aα,6,7,8,8a, 9,11,11a-undecahydro-3β,6α,9-trimethylfurano[3,4-j][1,2]benzodioxepin-9-carboxaldehyde (0.9 g) in ethanol (5 ml) a solution of silver nitrate (1.8 g) in water (3.0 ml) was added. To this stirred reaction mixture a solution of sodium hydroxide (0.4 g) in water (2.0 ml) was added dropwise. The reaction mixture was stirred for further 2 hours at room temperature. The residue was then filtered and washed with 5.0 ml of aqueous alcohol. Alcohol was removed from the combined filtrate, under vacuum. The aqueous layer was diluted with water and extracted with chloroform (2×10 ml). The aqueous layer was then acidified with acetic acid. Extraction of the acidified layer followed by concentration of extract and crystallisation from isopropyl ether—petroleum ether gave the title product; 0.72 g (75.79%) m.p. 166°–167° C.

EXAMPLE 5

3α,11α-Epoxy-3,4,5,5aα,6,7,8,8a,9,11,11a-undecahydro-9-(2-propynoxy)methyl-3β,6α,9-trimethylfurano[3,4-j][1,2benzodioxepin To the stirred, ice cold, suspension of NaH (20 mg) in DMF (0.5 ml), propargyl bromide (0.1 ml) and 3α,11α-Epoxy-3,4,5,5aα,6,7,8,8a,9,11,11a-undecahydro-9-hydroxymethyl-3β,6α,9-trimethylfurano[3,4-j][1,2]benzodioxepin (60 mg) were added. The reaction mixture was slowly brought to room temperature and stirred for 2 hr. Water was then added to the reaction mixture and the product was extracted in petroleum ether (60°–80° C.). The product was purified by flash chromatography over silica gel; m.p. 105° C., yield 71%. Similarly following compounds were prepared, using appropriate halide in place of propargyl bromide.

3α,11α-Epoxy-3,4,5,5aα,6,7,8,8a,9,11,11a-undecahydro-9-(N,N-diethylaminoethoxy)methyl-3β,6α,9-trimethylfurano[3,4-j][1,2]benzodioxepin, an oil, yield 47%.

3α,11α-Epoxy-3,4,5,5aα,6,7,8,8a,9,11,11a-undecahydro-9-(2-propenoxy)methyl-3β,6α,9-trimethylfurano[3,4-j][1,2]benzodioxepin, an oil, yield 45%.

3α,11α-Epoxy-3,4,5,5aα,6,7,8,8a,9,11,11a-undecahydro-9-(3-phenyl-2-propenyloxy)methyl-3β,6α,9-trimethylfurano[3,4-j][1,2]benzodioxepin, an oil, yield 42%.

EXAMPLE 6

3α,11α-Epoxy-3,4,5,5aα,6,7,8,8a9,11,11a-undecahydro-9-(chloroacetoxy)methyl-3β,6α,9-trimethylfurano[3,4-j][1,2]benzodioxepin To the stirred solution of dimethylaminopyridine (DMAP) (0.1 g) in chloroform at room temperature chloroacetylchloride (0.1 ml) was added. The resulting mixture was stirred for 20 mins and then 3α,11α-epoxy-3,4,5,5aα,6,7,8,8a,11,11a-undecahydro-9-hydroxymethyl-3β,6α,9-trimethylfurano[3,4-j][1,2]benzodioxepin (0.07 g) was added. The reaction mixture was stirred for further 3 hrs. Water was added to the reaction mixture and the product was extracted in petroleum ether. The petroleum ether extract was washed with dil. HCl, water, dried (Na$_2$SO$_4$) and solvent removed. The product when purified by flash chromatography over silica gel was obtained, as an oil, yield 42%.

Similarly following compounds were prepared using appropriate acid chloride in place of chloroacetylchloride.

3α,11α-Epoxy-3,4,5,5aα,6,7,8,8a,11,11a-undecahydro-9-(4-chlorobutyryloxy)methyl-3β,6α,9-trimethylfurano[3,4-j][1,2]benzodioxepin, an oil, yield 35%.

EXAMPLE 7

Preparation of
3α,11α-Epoxy-3,4,5,5aα,6,7,8,8a,9,11,11a-undecahydro-9-methylsulfonyloxymethyl-3β,6α,9-trimethylfurano[3,4-j][1,2benzodioxepin A mixture of 3α,11α-epoxy-3,4,5,5aα,6,7,8,8a,11,11a-undecahydro-9-hydroxymethyl-3β,6α,9-trimethylfurano[3,4-j][1,2]benzodioxepin (0.06 g) and methanesulfonylchloride (0.1 ml) in pyridine (0.3 ml) was heated at 90°-100° C. for hrs. The reaction mixture was then cooled, diluted with water and the product was extracted with ethyl acetate. The ethyl acetate extract was washed with diluted acetic acid, water, aqueous sodium bicarbonate, water, dried (Na$_2$SO$_4$) and solvent removed to get an oil. The product was purified by flash chromatography over silica gel.

Similarly following sulfonate esters were prepared using appropriate sulfonyl chlorides in place of methylsulfonylchloride.

3α,11α-Epoxy-3,4,5,5aα,6,7,8,8a,11,11a-undecahydro-9-(p-toluenesulfonyloxy)methyl-3β,6α,9-trimethylfurano[3,4-j][1,2]benzodioxepin, an oil, yield 33%.

3α,11α-Epoxy-3,4,5,5aα,6,7,8,8a,11,11a-undecahydro-9-(phenylsulfonyloxy)methyl-3β,6α,9-trimethylfurano[3,4-j][1,2]benzodioxepin, an oil, yield 27%.

EXAMPLE 8

3α,11α-Epoxy-3,4,5,5aα,6,7,8,8a,11,11a-undecahydro-9-(4-chlorophenylaminothiocarbonyloxy)methyl-3β,6α,9-trimethylfurano[3,4-j][1,2]benzodioxepin A mixture of 3α,11α-Epoxy-3,4,5,5aα,6,7,8,8a,11,11a-undecahydro-9-hydroxymethyl-3β,6α,9-trimethylfurano[3,4-j][1,2]benzodioxepin (0.1 g) and 4-chlorophenylisothiocyanate (0.15 g) in pyridine was heated at 60° C. for 14 hrs. The reaction mixture was then cooled, diluted with water and extracted with petroleum ether (60°-80° C.). The combined extract was washed with diluted ice cold HCl, water, dried (Na$_2$SO$_4$) and solvent removed. The product was purified by flash chromatography over silica gel, m.p. 89°-90° C., yield 65%.

Similarly the following compounds were prepared using appropriate isocyanate or isothiocyanate in place of 4-chlorophenylisothiocyanate.

3α,11α-Epoxy-3,4,5,5aα,6,7,8,8a,11,11a-undecahydro-9-(4-chlorophenylaminocarbonyloxy)methyl-3β,6α,9-trimethylfurano[3,4-][1,2]benzodioxepin, mp. 160° C., yield 42%.

3α,11α-Epoxy-3,4,5,5aα,6,7,8,8a,11,11a-undecahydro-9-(4-fluorophenylaminothiocarbonyloxymethyl)-3β,6α,9-trimethylfurano[3,4-j][1,2]benzodioxepin, mp. 79°-80° C., yield 37%.

3α,11α-Epoxy-3,4,5,5aα,6,7,8,8a,11,11a-undecahydro-9-(2-propenylaminothiocarbonyloxymethyl)-3β,6α,9-trimethylfurano[3,4-j][1,2]benzodioxepin, an oil, yield 23%.

EXAMPLE 9

Preparation of
3α,11α-Epoxy-3,4,5,5aα,6,7,8,8a,11,11a-undecahydro-9-(4-trifluoromethylphenylmethylaminocarboxamido)-3β,6α,9-trimethylfurano[3,4-j][1,2]benzodioxepin To the stirred solution of 3α,11α-Epoxy-3,4,5,5aα,6,7,8,8a, 11,11a-undecahydro-3β,6α,9-trimethylfurano[3,4-j][1,2]benzodioxepin-9-carboxylic acid (0.07 g) in dry ethyl acetate (2.5 ml), thionyl chloride (0.1 ml) was added dropwise. The reaction mixture was stirred for half an hour and then solution of 4-trifluoromethylbenzylamine (0.2 ml) in dry ethyl acetate (2 ml) was added with cooling in ice-water bath. The reaction mixture was stirred for further half an hour at 60°-70° C., water was added, product was extracted with petroleum ether (60-80). Combined extract was washed repeatedly with water, dried and solvent removed. The residue obtained was repeatedly extracted with hot n-pentane to get the product amide, mp. 170°-172° C., yield 25%.

Similarly the following amides were prepared using appropriate amines in place of 4-trifluoromethylbenzylamine.

3α,11α-Epoxy-3,4,5,5aα,6,7,8,8a,9,11,11a-undecahydro-9-(N-morpholinoyl)-3β,6α,9-trimethylfurano[3,4-j][1,2]benzodioxepin, an oil, yield 43%.

3α,11α-Epoxy-3,4,5,5aα,6,7,8,8a,9,11,11a-undecahydro-9-(N-methylpiperazinoyl)-3β,6α,9-trimethylfurano[3,4-j][1,2]-benzodioxepin, mp. 93° C., yield 43%.

EXAMPLE 10

Preparation of 2-Chloroethyl 3α,11α-epoxy-3,4,5,5aα,6,7,8,8a, 9,11,11a-undecahydro-3β,6α,9-trimethylfurano[3,4-j][1,2]benzodioxepin-9-carboxylate To the stirred solution of 3α,11α-Epoxy-3,4,5,5aα,6,7,8,8a, 9,11,11a-undecahydro-3β,6α,9-trimethylfurano[3,4-j][1,2]benzodioxepin-9-carboxylic acid (0.05 g) in dry ethyl acetate (2 ml), thionylchloride (0.1 ml) was added dropwise. The reaction mixture was stirred for half an hour and then solution of pyridine (0.2 ml) in dry ethyl acetate was added, with cooling. The reaction mixture was stirred for 15 minutes and then 2-chloroethanol (0.2 ml) was added. The reaction mixture was stirred for further 1 hr, water was added and the product extracted with dichloromethane. The extract was washed with water, cold diluted HCl, water, dried (Na$_2$SO$_4$) and solvent removed. The product was purified by flash chromatography over silica gel, mp. 112° C., yield 46%.

Similarly the following esters were prepared using appropriate alcohol in place of 2-chloroethanol.

2-Propenyl 3α,11α-epoxy-3,4,5,5aα,6,7,8,8a,9,11,11a-undecahydro-3β,6α,9-trimethylfurano[3,4-j][1,2]benzodioxepin-9-carboxylate, an oil, yield 38%.

2-Bromoethyl 3α,11α-epoxy-3,4,5,5aα,6,7,8,8a,9,11,-11a-undecahydro-3β,6α,9-trimethylfurano[3,4-j][1,2]benzodioxepin-9-carboxylate, an oil, yield 47%.

3-Chloropropyl 3α,11α-epoxy-3,4,5,5aα,6,7,8,8a,9,11,-11a-undecahydro-3β,6α,9-trimethylfurano[3,4-j][1,2]benzodioxepin-9-carboxylate, an oil, yield 24%.

Ethyl 3α,11α-epoxy-3,4,5,5aα,6,7,8,8a,9,11,11a-undecahydro-3β,6α,9-trimethylfurano[3,4-j][1,2]benzodioxepin-9-carboxylate, an oil, yield 29%.

8-Chlorooctyl 3α,11α-epoxy-3,4,5,5aα,6,7,8,8a,9,11,-11a-undecahydro-3β,6α,9-trimethylfurano[3,4-j][1,2]benzodioxepin-9-carboxylate, an oil, yield 21%.

EXAMPLE 11

Preparation of
1-(3α,11α-Epoxy-3,4,5,5aα,6,7,8,8a,9,11,11a-undecahydro-3β,6α,9-trimethylfurano[3,4-j][1,2]benzodioxepin-9-yl)-2,2'-dicarboethoxyethylene A mixture of 3α,11α-Epoxy-3,4,5,5aα,6,7,8,8a,9,11,-11a-undecahydro-3β,6α,9-trimethylfurano[3,4-j][1,2]benzodioxepin-9-carboxaldehyde (0.08 g) diethyl malonate (0.3 ml), pyridine (0.3 ml) and piperidine (1.0 ml) was heated with stirring at 80° C. for 16 hrs. The reaction mixture was cooled, treated with diluted HCl and was then extracted with petroleum ether (60-80). The extract was washed with water, dried ($Na_2SO_4$) and solvent removed. The residue was flash chromatographed over silica gel to get the title compound, as an oil, yield 22%.

EXAMPLE 12

Preparation of
3α,11α-Epoxy-3,4,5,5aα,6,7,8,8a,9,11,11a-undecahydro-9-(cis-4-trifluoromethylstyryl)-3β,6α,9-trimethylfurano[3,4-j][1,2]benzodioxepin To the stirred solution of the triphenyl p-trifluoromethylbenzyl phosphonium bromide (0.18 g) in dry tetrahydrofuran (2 ml), sodium hydride (0.03 g) was added. The reaction mixture was stirred for 30 mins at room temperature. 3α,11α-Epoxy-3,4,5,5aα,6,7,8,-,8a,9,11,11a-undecahydro-3β,6α,9-trimethylfurano[3,4-j][1,2]benzodioxepin-9-carboxaldehyde (5) (0.09 g) was then added to the above phosphonium ylide and the reaction mixture stirred for further 2 hrs. Water was then added to the reaction mixture and product extracted with chloroform. Residue from concentration of chloroform extract was purified by flash chromatography over silica gel, using chloroform as an eluant, first gave trans product in 9% yield. Further elution gave cis product in 26% yield.

Similarly following the conditions described using triethyl phosphonoacetate in place of triphenyl p-trifluoromethylbenzyl phosphonium bromide, the compound cis-1-(3α,11α-epoxy-3,4,5,5aα,6,7,8,8a,9,11,11a-undecahydro-3β,6α,9-trimethylfurano[3,4-j][1,2]benzodioxepin-9-yl)-2-carboethoxyethylene was obtained as an oil, yield 54%.

EXAMPLE 13

Preparation of
3α,12α-Epoxy-3,4,5,5aα,6,7,8,8aα,9,10,12β,12a-dodecahydro-10α-[3α,11α-epoxy-3,4,5,5aα,6,7,8,8a,-9,11,11a-undecahydro-3β,6α,9-trimethylfurano[3,4-j][1,2]benzodioxepin-9-methylene]oxy-3β,6α,9β-trimethylpyrano[4,3-j][1,2]benzodioxepin To a solution of dihydroartemisinin (0.490 g; 1.70 mmol) and 3α,11α-Epoxy-3,4,5,5aα,6,7,8,8a,9,11,11a-undecahydro-9-hydroxymethyl-3β,6α,9-trimethylfurano[3,4-j][1,2]benzodioxepin (0.350 gm; 1.23 mmol) in dry methylenechloride (70.0 ml) borontrifluoride etherate (0.2 ml) was added dropwise at 0° C. Reaction mixture was stirred for 15 minutes and then washed with water. The organic layer was separated, dried, filtered and filtrate was concentrated. Residue obtained after concentration, was purified by flash chromatography using silica gel column to obtain the product. mp. 100° C., yield 21%.

EXAMPLE 14

Preparation of
3α,12α-Epoxy-3,4,5,5aα,6,7,8,8aα,9,10,12β,12a-dodecahydro-10β-[3α,11α-epoxy-3,4,5,5aα,6,7,8,8a-,9,11,11a-undecahydro-3β,6α,9-trimethylfurano[3,4-j][1,2]benzodioxepin-9-methylen]oxy-3β,6α,9β-trimethylpyrano]4,3-j][1,2]benzodioxepin To a solution of dihydroartemisinin (0.490 gm; 1.70 mmol) and 3α,11α-Epoxy-3,4,5,5aα,6,7,8,8a,9,11,11a-undecahydro-9-hydromethyl-3β,6α,9-trimethylfurano[3,4-j][1,2]benzodioxepin (0.350 gm; 1.23 mmol) in dry methylenechloride (70.0 ml), borontrifluorideetherate (0.2 ml) was added drop wise at 0° C. Reaction was stirred for 15 minutes and then washed with water. The organic layer was separated, dried, filtered and filtrate was concentrated. Residue obtained after concentration, was purified by flash chromatography using silica gel column. The first few fractions of α-isomer were discarded. Further elution gave the fractions containing the title compound pure product, mp 154°-156° C., yield 34%.

We claim:

1. Compound of formula I

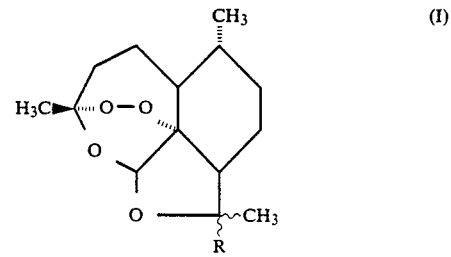

wherein R stands for:
CHO;
$COOR_1$,
wherein $R_1$ stands for hydrogen, alkyl, substituted alkyl, alkenyl, substituted alkenyl, alkynyl, or substituted alkynyl group;
$CH_2OR_2$,
wherein $R_2$ stands for hydrogen, alkyl, substituted alkyl, alkenyl, substituted alkenyl, alkynyl, substituted alkynyl, dialkylamino alkyl group, or 3α,12α-Epoxy-3,4,5,5aα,6,7,8,8aα,9,10,12β,12a-dodecahydro-3β,6α,9β-trimethyl-pyrano[4,3-j][1,2]benzodioxepin-10-yl, or a group $COR_3$, wherein $R_3$ stands for alkyl, substituted alkyl group, or a group $SO_2R_4$, wherein $R_4$ stands for alkyl or aryl group, or a group

wherein X denotes O or S,
$R_5$ stands for hydrogen,
$R_5'$ stands for alkyl or aryl group or
$NR_5R_5'$, stands for heterocycle of 5 to 6 members;
$CONR_6R_7$,
wherein $R_6$ stands for hydrogen or aralkyl, $R_7$ stands for hydrogen, alkyl, aryl or aralkyl group, or $R_6$ and $R_7$ together with the nitrogen to which they are attached form a heterocycle of 5 to 6 members which may contain an additional hetero atom and is unsubstituted or substituted at one or more places by alkyl, alkoxy, hydroxy, halogen, or aryl groups;
$CH=CR_8R_9$,
wherein $R_8$ stands for hydrogen or carboxyalkyl, and $R_9$ stands for carboxyalkyl, aryl or heterocycle wherein aryl stands for a phenyl group which is optionally substituted by one or more substituents selected from halogen, alkyl, nitro, amino, hydroxy, alkoxy, carboxy, alkylcarboxylate, trifluoromethyl, substituted amino, acetyl, alkenyloxy, or alkynyloxy and wherein heterocycle stands for a cyclic group containing one or more hetero atoms selected from piperazino, morpholino, piperidino, pyrrolidino, phthalimide, optionally substituted at one or more places by alkyl, alkoxy, hydroxy, halogen, or aryl groups;

$COSR_{10}$, wherein $R_{10}$ stands for alkyl, substituted alkyl, or aryl groups;

and pharmaceutically acceptable salts thereof.

2. Compounds of formula I as claimed in claim 1, wherein R stands for CHO or $CH_2OR_2$, $R_2$ denoting hydrogen, alkyl, substituted alkyl, alkenyl, substituted alkenyl, alkynyl, substituted alkynyl, dialkylamino alkyl group or 3α,12α-Epoxy-3,4,5,5aα,6,7,8,8aα,9,10,12β,-12a-dodecahydro-3β,6α,9β-trimethylpyrano[4,3-j][1,2]benzodioxepin-10-yl or a group $COR_3$, wherein $R_3$ stands for alkyl, substituted alkyl group, or a group $SO_2R_4$, wherein $R_4$ stands for alkyl or aryl group, or a group $CNR_5R_5'$,
$\|$
$X$ wherein X denotes O or S.

3. Compounds as claimed in claim 1 which are
3α,11α-Epoxy-3,4,5,5aα,6,7,8,8a,9,11,11a-undecahydro-9-formyl-3β,6α,9-trimethylfurano[3,4-j][1,2]benzodioxepin,
3α,11α-Epoxy-3,4,5,5aα,6,7,8,8a,9,11,11a-undecahydro-9-(2-propynoxy)methyl-3β,6α,9-trimethylfurano[3,4-j][1,2]benzodioxepin,
3α,11α-Epoxy-3,4,5,5aα,6,7,8,8a,9,11,11a-undecahydro-9-(2-propenoxy)methyl-3β,6α,9-trimethylfurano[3,4-j][1,2]benzodioxepin,
3α,11α-Epoxy-3,4,5,5aα,6,7,8,8a,9,11,11a-undecahydro-9-(p-toluenesulfonyloxy)methyl-3β,6α,9-trimethylfurano[3,4-j][1,2]benzodioxepin,
3α,11α-Epoxy-3,4,5,5aα,6,7,8,8a,9,11,11a-undecahydro-9-(4-chlorophenylaminothiocarbonyloxy)methyl-3β,6α,9-trimethylfurano[3,4-j][1,2]benzodioxepin,
3α,11α-Epoxy-3,4,5,5aα,6,7,8,8a,9,11,11a-undecahydro-9-(4-fluorophenylaminothiocarbonyloxy)methyl-3β,6α,9-trimethylfurano[3,4-j][1,2]benzodioxepin,
3α,12α-Epoxy-3,4,5,5aα,6,7,8,8aα,9,10,12β,12 a-dodecahydro-10α-[3α,11α-epoxy-3,4,5,5aα,6,7,8,8a,9,11,11a-undecahydro-3β,6α,9-trimethylfurano[3,4-j][1,2]benzodioxepin-9-methylen]oxy-3β,6α,9β-trimethylpyrano[4,3-j][1,2]benzodioxepin und
3α,12α-Epoxy-3,4,5,5aα,6,7,8,8aα,9,10,12β,12a-dodecahydro-10β-[3α,11α-epoxy-3,4,5,5aα,6,7,8,8a,9,10,11,11a-undecahydro-3β,6α,9-trimethylfurnao[3,4-j][1,2]benzodioxepin-9-methylen]oxy-3β,6α,9β-trimethylpyrano[4,3-j][1,2]benzodioxepin.

4. A process for the production of compounds of the formula I as claimed in claim 1, wherein a compound of formula II

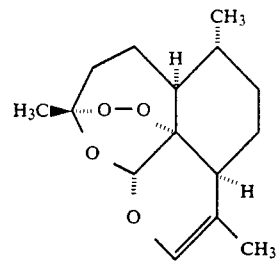

is treated with a brominating agent and subsequently hydrolyzed to a compound of formula III

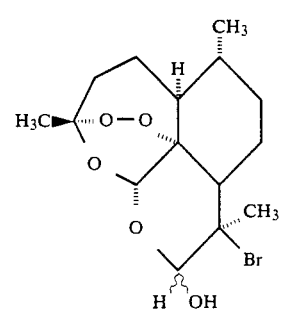

which is for the preparation of compounds of formula Ia

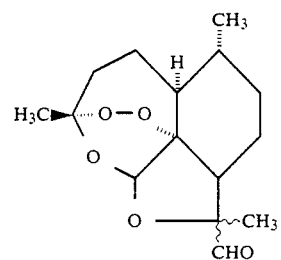

treated with an organic base, or wherein, for the preparation of compounds of formula Ib,

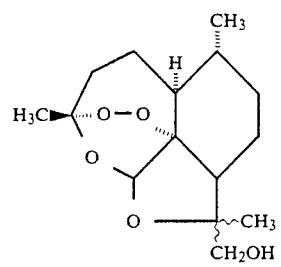

compounds of formula Ia are treated with a reducing agent, or wherein for the preparation of compounds of formula Ic

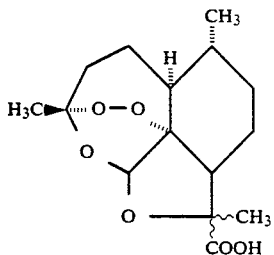

compounds of formula Ia are treated with an oxidizing agent or wherein for the preparation of compounds of formula Id

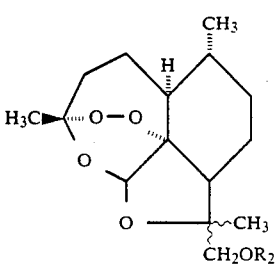

compounds of formula Ib are alkylated or are reacted with dihydroartemisine, or wherein for the preparation of compounds of formula Ie

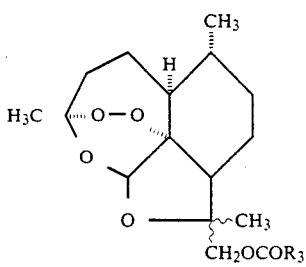

compounds of formula Ib are treated with acid chlorides of the formula $R_3COCl$, or wherein for the preparation of compounds of formula If

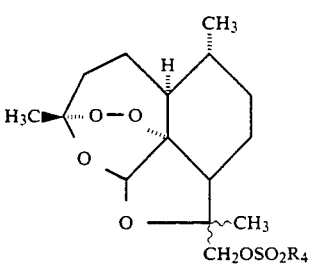

compounds of formula Ib are reacted with compounds of the formula $R_4SO_2Cl$ or wherein for the preparation of compounds of formula Ig

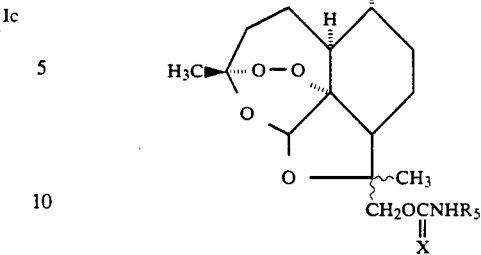

compounds of formula Ib are reacted with compounds of the formula $R_5NCX$, or wherein for the preparation of compounds of formula Ih

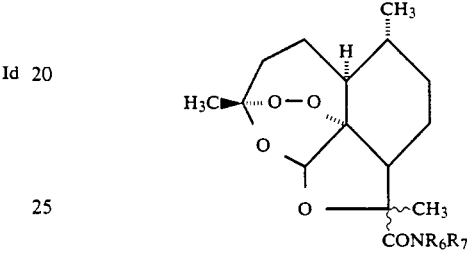

compounds of formula Ic are reacted with thionylchloride and subsequently with compounds of the formula $NR_6R_7$, or wherein for the preparation of compounds of the formula Ii

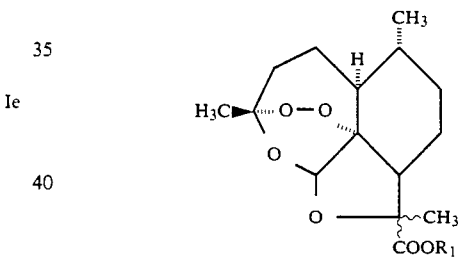

compounds of formula Ic are reacted with thionylchloride and subsequently with a compound of the formula $R_1OH$ or wherein for the preparation of compounds of the formula Ij

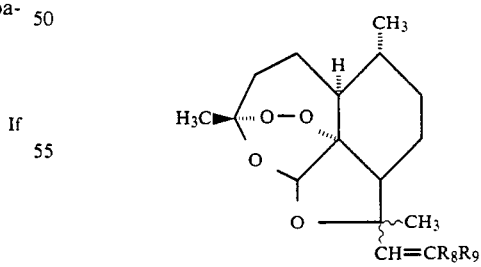

wherein $R_8$ and $R_9$ stand for carbethoxy a compound of the formula Ia is treated with compounds of the formula $CH_2R_8R_9$ or wherein for the preparation of compounds of the formula Ij, wherein $R_8$ stands for hydrogen and $R_9$ stands for carboalkyl, aryl or a heterocycle, a compound of the formula Ia is treated with compounds of the formula $Ph_3P=CHR_9$, the substituents $R_1-R_9$ having—where not especially defined—the same meanings as in the preceding claims.

5. A pharmaceutical which contains at least one of the compounds as claimed in claim 1, and a pharmaceutically acceptable carrier.

6. A method of treatment for malaria comprising administering an effective amount of the compound as claimed in claim 1, together with a pharmaceutically acceptable carrier, to a host.

7. A method of treatment for protozoal and viral infections, comprising administering an effective amount of the compound as claimed in claim 1, together with a pharmaceutically acceptable carrier, to a host.

* * * * *

UNITED STATES PATENT AND TRADEMARK OFFICE
CERTIFICATE OF CORRECTION

PATENT NO. : 5,246,930  
DATED : September 21, 1993  
INVENTOR(S) : Bindumadhavan Venugopalan et al.

Page 1 of 2

It is certified that error appears in the above-indentified patent and that said Letters Patent is hereby corrected as shown below:

TITLE PAGE

Abstract, last line, change "a" to --an--.

Claim 2, column 23, line 16, after "12B" delete "-".

Claim 3, column 23, line 53, change "12" to --12a- --.

Claim 3, column 23, line 54, delete "a-".

Claim 3, column 23, line 54, after "ep" insert -- - --.

Claim 3, column 23, line 58, change "und" to --and--.

Claim 3, column 23, line 59, change "12a-d" to --12a--.

Claim 3, column 23, line 60, change "odecahydro" to --dodecahydro--.

Claim 3, column 23, line 60, change "8a-" to --8a,--.

UNITED STATES PATENT AND TRADEMARK OFFICE
CERTIFICATE OF CORRECTION

PATENT NO. : 5,246,930
DATED : September 21, 1993
INVENTOR(S) : Bindumadhavan Venugopalan et al.

It is certified that error appears in the above-indentified patent and that said Letters Patent is hereby corrected as shown below:

Claim 3, column 23, line 61, delete "," (first occurrence).

Claim 4, column 26, line 61, after "carbethoxy" insert --,--.

Signed and Sealed this

Thirteenth Day of September, 1994

Attest:

BRUCE LEHMAN

Attesting Officer     Commissioner of Patents and Trademarks